United States Patent [19]

Sarantakis

[11] 3,997,517
[45] Dec. 14, 1976

[54] CYCLIC SOMATOSTATIN DISULFIDE ANALOGUES

[75] Inventor: Dimitrios Sarantakis, West Chester, Pa.

[73] Assignee: American Home Products Corporation, New York, N.Y.

[22] Filed: Jan. 30, 1976

[21] Appl. No.: 653,685

[52] U.S. Cl. .......................... 260/112.5 S; 424/177
[51] Int. Cl.² .............. C07C 103/52; A61K 37/00
[58] Field of Search .............. 260/112.5 S; 424/177

[56] References Cited

UNITED STATES PATENTS 3,931,140  1/1976  Sarantakis .................. 260/112.5 S Primary Examiner—Lewis Gotts
Assistant Examiner—Reginald J. Suyat
Attorney, Agent, or Firm—Richard K. Jackson

[57] ABSTRACT

Cyclized somatostatin analogues containing the Cys-Cys disulfide linkage, their pharmaceutically acceptable acid addition salts as well as their cyclic disulfhydryl precursors and intermediates therefor are disclosed. The cyclized analogues of somatostatin selectively reduce blood serum concentrations of growth hormone without materially affecting the concentrations of glucagon or insulin.

11 Claims, No Drawings

CYCLIC SOMATOSTATIN DISULFIDE ANALOGUES

BACKGROUND OF THE INVENTION

The structure of the growth hormone release inhibiting factor, somatostatin, has been determined by Brazeau et al., Science, 179, 77 (1973). Both solid phase and solution methods have been employed in the preparation of somatostatin. The structure of somatostatin is

```
H—Ala—Gly—Cys—Lys—Asn—Phe—Phe—
                  \
                   \
Trp—Lys—Thr—Phe—Thr—Ser—Cys—OH .
```

Many analogues of somatostatin have been prepared. For example, Rivier et al., Biochem. Biophys. Res. Comm., vol. 65, No. 2, pp. 746–751 (1975) disclose D-Trp$^8$-somatostatin. Additional analogues are disclosed in U.S. Pat. No. 3,904,594.

DESCRIPTION OF THE INVENTION

In accordance with this invention there is provided a group of cyclic somatostatin disulfide analogues of the formula:

```
S ————————— S
|           |
Cys—X₁—X₂—Cys—Lys—Asn—Phe
↑                       ↓
Ser—Thr—Phe—Thr—Lys—X₃—Phe
``` in which each of the identified optically active amino acid moieties is in the L-configuration;
$X_1$ is L-Ala, Gly-L-Ala, Gly$_2$-L-Ala, Gly$_3$-L-Ala, Gly-Gly, Gly-Gly-L-Tyr-L-Ala, D-Ala-Gly-Gly-L-Tyr, D-Phe-L-Phe$_3$ L-Ala,L-Phe$_3$-L-Ala or L-Phe-L-Phe;
$X_2$ is Gly, 2-methyl-Ala or L-Phe and
$X_3$ is L-Trp or D-Trp or a pharmaceutically acceptable acid addition salt thereof. These compounds inhibit the release of growth hormone from the pituitary gland without materially affecting blood serum concentrations of insulin or glucagon. This degree of specificity in control of growth hormone renders the compounds of this invention ideal for treatment of pathologies involving excessive growth hormone secretion where the endogenous levels of insulin and glucagon are not desireably affected. Thus, the compounds of this invention are useful in the treatment of acromegaly.

The preferred compounds are those in which $X_1$ in the structure depicted, supra, is L-Ala or Gly-Gly-L-Ala and $X_2$ is Gly.

By pharmaceutically acceptable acid addition salts, it is intended to embrace those salts derived from both inorganic and organic acids conventionally employed in pharmaceutical practice, such as hydrochloric, hydrobromic, sulfuric, polyphosphoric, phosphoric, maleic, acetic, citric, benzoic, succinic, malic, ascorbic acid, and the like.

The intermediates produced in preparation of the cyclic somatostatin disulfide analogues represent additional aspects of the invention. The intermediates are the cyclic Cys, Cys-disulfhydryl precursors and the protected C-terminal hydrazides.

The cyclic Cys, Cys-disulfhydryl precursors present the structural formula:

```
SH          SH
|           |
Cys—X₁—X₂—Cys—Lys—Asn—Phe
↑                       ↓
Ser—Thr—Phe—Thr—Lys—X₃—Phe
``` in which
X is L-Ala, Gly-L-Ala, Gly$_2$-L-Ala, Gly$_3$-L-Ala, Gly-Gly, Gly-Gly-L-Tyr-L-Ala, D-Ala-Gly-Gly-L-Tyr, D-Phe-L-Phe$_3$-L-Ala, L-Phe-$_3$-L-Ala or L-Phe-L-Phe;
$X_2$ is Gly, 2-methyl-Ala or L-Phe and
$X_3$ is L-Trp or D-Trp.

The protected C-terminal hydrazides present the formula:

(R)-Cys(R$^1$)-X$_1$-X$_2$-Cys(R$^2$)-Lys(R$_3$)-Asn-Phe-Phe-X$_3$-Lys(R$^4$)-Thr(R$^5$)-Phe-Thr(R$^6$)-Ser(R$^7$)-N$_2$H$_3$ wherein each of the designated optically active amino acid moieties is in the L-configuration;
R is hydrogen, formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2,-trichloroethoxycarbonyl, amyloxycarbonyl, α,α-dimethylbenzyloxycarbonyl, α,α-dimethyl-3,5-dimethoxy-benzyloxycarbonyl, benzhydryloxycarbonyl, 9-fluorenyl-methoxycarbonyl, isobornyloxycarbonyl, adamantyloxy-carbonyl;
R$^1$ and R$^2$ are protecting groups for the sulfhydryl group of the two cysteinyl moieties independently selected from the group consisting of benzyl, 3,4-dimethylbenzyl, p-methoxybenzyl, p-nitrobenzyl, p-chlorobenzyl, trityl, benzhydryl, tetrahydropyranyl, acetamidomethyl, t-butylthio, ethylthio, ethylcarbamoyl, benzylthiomethyl or benzoyl;
R$^3$ and R$^4$ is formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxy-carbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5dimethoxy-benzyloxycarbonyl, benzhydryloxycarbonyl, 9-fluorenyl-methoxycarbonyl, isobornyloxycarbonyl, adamantyloxy-carbonyl;
R$^5$, R$^6$and R$^7$ are protecting groups for the hydroxyl group of the threonyl and seryl moieties, independently selected from the group consisting of benzoyl, tert-butyl, benzyl;
X$_1$ is L-Ala, Gly-L-Ala, Gly$_2$-L-Ala, Gly$_3$-L-Ala, Gly-Gly, Gly-Gly-L-Tyr-L-Ala, D-Ala-Gly-Gly-L-Tyr,

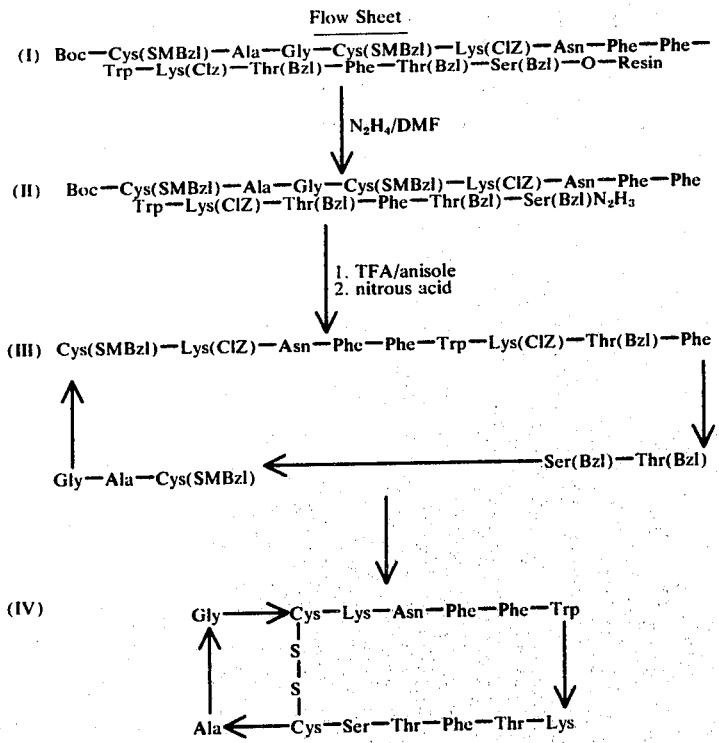

Flow Sheet

D-Phe-L-Phe₃-L-Ala, L-Phe₃-L-Ala or L-Phe-L-Phe;

X₂ is Gly, 2-methyl-Ala or L-Phe; and

X₃ is L-Trp or D-Trp.

The cyclic somatostatin disulfide analogues of this invention are prepared by a combination of solid phase and conventional peptide synthesis methods. The following flow sheet and specific examples illustrate the procedure followed in the production of cyclic somatostatin disulfide as the prototype for the other compounds embraced by this invention. It is to be understood that by changing the amino acid sequence of the polypeptide in accordance with the instructions provided by this disclosure, affords each of the compounds embraced by the description presented herein and embraced by the claims of this application. Cyclic somatostatin disulfide, being representative of the entire group of compounds disclosed herein in its preparation and ultimate activity is used to illustrate the invention and is not to be construed as a limitation thereof.

Thus, in explanation of the following flow sheet, the peptido resin (I) is prepared according to the usual and familiar methodology of solid phase synthesis [Stewart et al., Solid Phase Peptide Synthesis, Freeman and Co., San Francisco, 1969]. the peptido resin treated with hydrazine to obtain the protected tetradecapeptide hydrazide (II) which, after removal of the N α -t-butyloxycarbonyl group with trifluoroacetic acid (TFA), is cyclized by the azide method to give (III). The crude product is deprotected with liquid HF and oxidized at pH 7.4 by air to give (IV).

The symbols employed in the flow sheet correspond to the groups and reagents employed in the following working examples, representing the use of specific and preferred protective groups and reagent systems. It is to be understood that it is within the skill of this art to vary the specifics of the reactions depicted in the flow sheet widely, as taught elsewhere in this specification.

The resin support employed in the solid phase synthesis may be any suitable resin conventionally employed in the art for the solid phase preparation of polypeptides, preferably polystyrene which has been cross-linked with from 0.5 to about 3 percent divinyl benzene, which has been chloromethylated to provide sites for ester formation with the initially introduced fully protected seryl moiety. Following the coupling of the α-amino and hydroxyl protected serine to the resin support, the α-amino protecting group is removed by standard methods employing trifluoro-acetic acid in methylene chloride, trifluoroacetic acid alone or HCl in dioxane. The deprotection is carried out at a temperature between about 0° C. and room temperature. After removal of the α-amino protecting group the remaining protected amino acids are coupled, seriatim, in the desired order to obtain the desired product. Alternatively, multiple amino acid groups may be separately coupled by the solution method prior to coupling with the resin supported amino acid sequence. The selection of an appropriate coupling reagent is within the skill of the art. A particularly suitable coupling reagent is N,N¹-diisopropyl carbodiimide (DIC). Other applicable coupling agents are (1) carbodiimides (e.g. N,N¹-dicyclohexycarbodiimide, N-ethyl N¹-(α-dimethylamino propyl carbodiimide); (2) isoxazolium salts (e.g. N-ethyl-5-phenyl-isoxazolium-3'-sulfonate; (3) monocyclic nitrogen containing heterocyclic amides of aromatic character containing one through four nitrogens in the ring such as imidazolides, pyrazolides, 1,2,4-triazolides, specific heterocyclic amides that are useful include N,N'-carbonyl diimidazole, N,N'-carbonyl-di-1,2,4-triazole; (4) reagents which form a mixed anhydride with the carboxyl moiety of the amino acid (e.g. ethylchloroformate, isobutylchloroformate) and (5) nitrogen containing heterocyclic compounds having a hydroxy group on one ring nitrogen (e.g. N- hydroxyphthalimide, N-hydroxy-succinimide, 1-hydroxybenzotriazole. Other activating reagents and their use in peptide coupling are described by Schroder & Lubke supra, in Chapter III and by Kapoor, J. Pharm. Sci., 59, pp. 1–27, (1970).

Each protected amino acid or amino acid sequence is introduced into the solid phase reactor in about a four-fold excess and the coupling is carried out in a medium of dimethylformamide: methylene chloride (1:1) or in dimethylformamide or methylene chloride alone. In cases where incomplete coupling occurs the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34 595 (1970).

The in vivo activity of the cyclic somatostatin disulfide analogues of this invention was established with cyclic somatostatin disulfide as a representative member of the family of compounds by comparing the blood serum growth hormone, glucagon and insulin concentrations found in rats grouped for control, somatostatin and cyclic somatostatin disulfide comparison. The rats, weighing between 200 and 250 grams were treated with Nembutal, 50 milligrams per kilogram intraperitoneally. After five minutes the somatostatin, control and cyclic somatostatin disulfide administrations were made subcutaneously. The rats blood was sampled fifteen minutes later and the growth hormone, glucagon and insulin levels were determined by radioimmunoassay. The results of this were as follows:

| Compound | Dose μg/kg | GH ng/ml | Glucagon pg/ml | Insulin μg/ml |
| --- | --- | --- | --- | --- |
| Control | — | 291±47 | 33±2 | 272±39 |
| Somatostatin | 200 | 40±4* | 17±2* | 161±21+ |
| Example IV | 3000 | 40±4* | 29.7±4 | 308±30 |

*p < 0.01
+p < 0.05

From this data it is apparant that the compounds of this invention lower growth hormone concentrations in blood serum without affecting insulin or glucagon levels at a dose as high as 3 milligram/kilogram/animal.

Like somatostatin, the compounds of this invention are useful in the prevention of excessive secretion of growth hormone in domestic animals and the human. From the known relationship between growth hormone control in standard experimental animals and the human, the activity of the disclosed compounds characterizes them as useful in the treatment of acromegaly and juvenile diabetes in the same manner as somatostatin itself. Administration of the cyclic somatostatin disulfide analogues of this invention may be by conventional routes common to somatostatin and related polypeptides, under the guidance of a physician, orally or parenterally, in an amount dictated by the extent of the dysfunction as determined by the physician. The compounds may be administered alone or in conjunction with conventional pharmaceutically acceptable carriers and adjuvants, in unit dosage form containing from about 1.0 to about 100 milligrams per kilogram host body weight.

EXAMPLE 1

N-tert-butyloxycarbonyl-S-p-methoxybenzyl-L-cysteinyl-L-alanyl-glycyl-S-p-methoxybenzyl-L-cysteinyl-ε-2-chlorobenzyloxycarbonyl-L-lysyl-L-asparaginyl-L-phenylalanyl-L-phenylalanyl-L-tryptophyl-ε-2-chlorobenzyloxycarbonyl-L-lysyl-O-benzyl-L-threonyl-L-phenyl-alanyl-O-benzyl-L-threonyl-O-benzyl-L-seryl-hydroxymethyl-polystyrene.

The above titled peptido resin is prepared from chloromethylated polystyrene cross-linked 1% with p-divinyl-benzene. The first protected amino acid Boc-o-benzyl-L-serine is esterified with the resin by Gisin's method, using its cesium salt [Gisin, Helv. Chim. Acta, 56, 1476 (1973)]. The polystyrene resin ester is analyzed by quantitative amino acid analysis and after correction for decomposition of part of serine the substitution is determined. In this example, substitution was found to be 0.500 m moles/ g resin. This resin ester was then treated according to Schedule A for the incorporation of, Boc-Thr(Bzl)OH, Boc-Phe-OH, Boc-Thr(Bzl)-OH, Boc-Lys(ClZ)-OH, Boc-Trp-OH, Boc-Phe-OH, Boc-Phe-Oh, Boc-Asn-OH, Boc-Lys(ClZ)-OH, Boc-Cys(SMBzl)-OH, Boc-Gly-OH, Boc-Ala-OH, and Boc-Cys(SMBzl)-OH. The other analogues polypeptides described, supra, are prepared by substituting the appropriate amino acid(s) in the proper preparatory sequence. For example, D-Boc-Trp-OH is substituted for L-Boc-Trp-OH to afford the D-Trp analogue. During the coupling of each of the above amino acids, one equivalent of N-hydroxybenzotriazole was added in order to accelerate the reaction.

Schedule A

1. Wash with $CH_2Cl_2$ × 3
2. Treat with $TFA-CH_2Cl_2$ -DTE (1:2:0.5%) for 5 min.
3. Treat with $TFA-CH_2Cl_2$ -DTE (1;2;0.5%) for 25 min.
4. Wash with $CH_2Cl_2$ × 3
5. Wash with DMF
6. Treat with 12% TEA in DMF twice for 3 minutes
7. Wash with DMF
8. Wash with $CH_2Cl_2$ × 3
9. Treat with 4 equivalents of the corresponding amino acid derivative in $CH_2Cl_2$ - DMF and 4 equivalents of N-hydroxybenzotriazole and stir for 5 minutes
10. Add in two portions 5 equivalents of DIC dissolved in $CH_2Cl_2$ and over a period of 30 minutes. Reaction time 12–18 hours.
11. Wash with DMF × 3
12. Wash with $CH_2Cl_2$ × 3
13. Test ninhydrin reaction according to Kaiser et al., Annal. Biochem. 34, 595 (1970). In case of incomplete reaction repeat lines 9 to 14 as above.

During the addition of Boc-Asn-OH a two fold quantity of N-hydroxy-benzotriazole over the normal, i.e., 8 equivalents, was added.

EXAMPLE II

N-tert-butyloxycarbonyl-S-p-methoxybenzyl-L-cysteinyl-L-alanyl-glyclyl-S-p-methoxy-benzyl-L-cysteinyl-ε-2-chlorobenzyloxycarbonyl-L-lysyl-L-asparaginyl-L-phenylalanyl-L-phenylalanyl-L-tryptophyl-ε-2-chlorobenzyloxycarbonyl-L-lysyl-O-benzyl-L-threonyl-L-phenylalanyl-O-benzyl-L-threonyl-O-benzyl-L-seryl-hydrazide.

The peptidoresin of the previous example (27.3 g.) was suspended in 300 ml. DMF and then hydrazine anhydrous (40 ml.) was added and the mixture was stirred at room temperature overnight. The reaction mixture was filtered and filtrate was evaporated to a small volume then water was added to give a white precipitate which after 2 hours standing, was collected and washed well with water, then dried over $P_2O_5$. Yield 16.6 g.

EXAMPLE III

Cyclo-S-p-methoxybenzyl-L-cysteinyl-L-alanyl-glycyl-S-p-methoxy-benzyl-ε-2-chlorobenzyloxycarbonyl-L-lysyl-L-asparaginyl-L-phenylalanyl-L-phenylalanyl-L-tryptophyl-ε-2-chlorobenzyloxy-carbony-L-lysyl-O-benzyl-L-threonyl-L-phenylalanyl-O-benzyl-L-threonyl-O-benzyl-L-serine.

The tetradecapeptide hydrazide of the previous example (7.81 g. 3 m moles) was mixed with anisole (15 ml.) acid treated with TFA (125 ml). The mixture is stirred for 30 minutes then the excess TFA is removed in vacuo and the residue is flash evaporated twice with dry ether. The residue is triturated with excess dry ether and the solid collected and dried to give 7.4 g. off-white material. This material was dissolved in 150 ml. DMF cooled at 20° C., then 3 equivalents of 4N HCl/EtOAc (2.1 ml.) was added followed by isoamyl nitrite (0.57 ml.) and the mixture was stirred for 12 minutes at −20° C., after which time the solution was poured into (1500ml.) DMF kept at −20° C. and containing 6 equivalents of $NEt_3$ (0.82 ml.). The reaction mixture was kept at −3° C. for 2 hours and at 0° to 5° C. for 3 days, then evaporated to a small volume and treated with excess of water to give, after 1 hour, 9 white solid, which was washed with water, 10% $KHCO_3$, 10% citric acid, and water, than dried over $P_2O_5$. Yield 6 g.

EXAMPLE IV

Cyclo-L-cysteinyl-L-alanyl-glycyl-L-cysteinyl-L-lysyl-L-asparaginyl-L-phenyl-alanyl-L-phenylalanyl-L-tryptophyl-L-lysyl-L-threonyl-L-phenylalanyl-L-threonyl-L-serine (1–4 disulfide).

The material of the previous example (6 g.) was treated with liquid HF (150 ml.) in the presence of anisole (10 ml.) for 45 minutes in an ice-bath. The excess HF was removed in vacuo as fast as possible and the residue was taken in 2 M-AcOH (dearated) (ca. 200 ml.) and washed with ether. The aqueous layer was evaporated in vacuo and the residue was dissolved in some dearated water and added to 4,000 ml. water and it was left to stand in the open air for 2 days (until no free SH was present) after the pH was adjusted to 7.4. The solution was acidified with gl. AcOH to pH 6.5 and lyophilized to yield 4.6 of a fluffy solid. Part of the crude material (4.5 g.) was chromatographed through Sephadex 625, column (2.5 × 200 cm.) and eluted with 1 M-AcOH. The material which emerged between 406 and 700 ml., 1,2 g., was chromatographed again through a Sephadex G-15 column (2.5 × 160 cm cm) and eluted with 1 M-AcOH. The compound which emerged between 496 ml. and 800 ml. (177.6 mg.) was lyophilized to give a white fluffy solid (Wy-40,391).

$R_f$ 0.56 (n-butanol-water-gl. AcOH, 10:2:1)

$R_f$ 0.74 (n-butanol-water-gl. AcOH-pyridine)

Amino acid analysis, Asp (1) 0.95, Thr(2) 1.89, Ser (1)0.89, Gly (1) 0.89, Ala (1) 0.90, Cys (2) 1.53, Phe (3) 3, Lys (2) 1.90, $NH_3$ (1) 1.59, Trp (1) 0.48.

What is claimed is:

1. A compound of the formula:

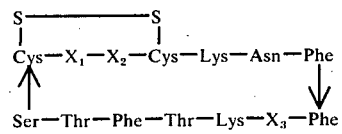

in which each of the identified optically active amino acid moieties is in the L-configuration;

X₁ is L-Ala, Gly-L-Ala, Gly₂-L-Ala, Gly₃-L-Ala, Gly-Gly, Gly-Gly-L-Tyr-L-Ala, D-Ala-Gly-Gly-L-Tyr, D-Phe-L-Phe₃-L-Ala, L-Phe₃-L-Ala or L-Phe-L-Phe;

X₂ is Gly, 2-methyl-Ala or L-Phe; and

X₃ is L-Trp or D-Trp, or a pharmaceutically acceptable acid addition salt thereof.

2. A compound of claim 1 in which

X₁ is L-Ala or Gly-Gly-L-Ala;

X₂ is Gly; and

X₃ is L-Trp or D-Trp, or a pharmaceutically acceptable acid addition salt thereof.

3. The compound of claim 1 which is

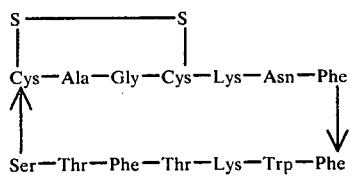

wherein each of the optically active amino acid moieties is in the L-configuration or a pharmaceutically acceptable acid addition salt thereof.

4. The compound of claim 1 which is

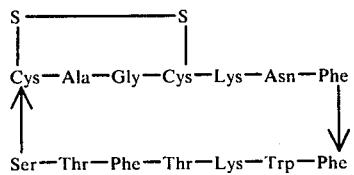

wherein Trp is D-tryptophyl and each of the other optically active amino acid moieties is in the L-configuration, or a pharmaceutically acceptable acid addition salt thereof.

5. A compound of the formula:

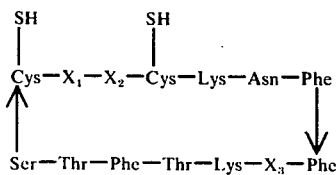

in which
X₁ is L-Ala, Gly-L-Ala, Gly₂-L-Ala, Gly₃-L-Ala, Gly-Gly, Gly-Gly-L-Tyr-L-Ala, D-Ala-Gly-Gly-L-Tyr, D-Phe-L-Phe₃-L-Ala, L-Phe₃-L-Ala or L-Phe-L-Phe;
X₂ is Gly, 2-methyl-Ala or L-Phe; and
X₃ is L-Trp or D-Trp,
or a pharmaceutically acceptable acid addition salt thereof.

6. A compound of claim 5 in which
X₁ is L-Ala or Gly-Gly-L-Ala;
X₂ is Gly; and
X₃ is L-Trp or D-Trp, or a pharmaceutically acceptable acid addition salt thereof.

7. The compound of claim 5 which is

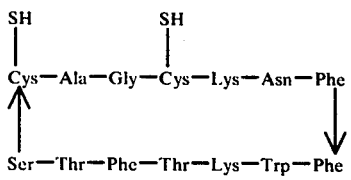

wherein each of the optically active amino acid moieties is in the L-configuration.

8. The compound of claim 5 which is

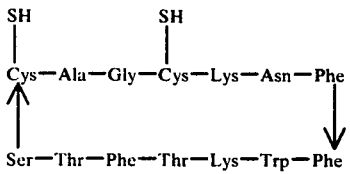

wherein Trp is D-tryptophyl and each of the other optically active amino acid moieties is in the L-configuration.

9. A compound of the formula:

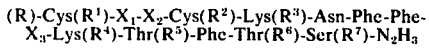

wherein each of the designated optically active amino acid moieties is in the L-configuration;

R is hydrogen, formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxy-carbonyl diisopropylmethoxycarbonyl, allyloxycarbonyl, 2,2,2-trichloroethoxycarbonyl, amyloxycarbonyl, α, α-dimethylbenzyloxycarbonyl, α,α-dimethyl-3,5-dimethoxy-benzyloxycarbonyl, benzhydryloxycarbonyl, 9-fluorenylmethoxycarbonyl, isobornyloxycarbonyl, adamantyloxycarbonyl.

R¹ and R² are protecting groups for the sulfhydryl group of the two cysteinyl moieties independently selected from the group consisting of benzyl, 3,4-dimethylbenzyl, p-methoxybenzyl, p-nitrobenzyl, p-chlorobenzyl, trityl, benzhydryl, tetrahydropyranyl, acetamidomethyl. t-butylthio, ethylthio, ethylcarbamoyl, benzylthiomethyl or benzoyl;

R³ and R⁴ is formyl, trifluoroacetyl, phthalyl, toluene sulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluorenylmethoxycarbonyl, isobornyloxycarbonyl, adamantyloxycarbonyl.

R⁵, R⁶ and R⁷ are protecting groups for the hydroxyl group of the threonyl and seryl moieties, independently selected from the group consisting of benzoyl, tert-butyl, benzyl;

X₁ is L-Ala, Gly-L-Ala, Gly₂-L-Ala, Gly₃-L-Ala, Gly-Gly, Gly-Gly-L-Tyr-L-Ala, D-Ala-Gly-Gly-L-Tyr, D-Phe-L-Phe₃-L-Ala, L-Phe₃-L-Ala or L-Phe-L-Phe;
X₂ is Gly, 2-methyl-Ala or L-Phe; and
X₃ is L-Trp or D-Trp.

10. The compound of claim 9, in which X₁ is L-Ala; X₂ is Gly and X₃ is L-Trp.

11. The compound of claim 10 in which R is t-butyloxycarbonyl; R¹ is p-methoxybenzyl; R² is p-methoxybenzyl; R³ is 2-chlorobenzyloxycarbonyl; R⁴ is 2-chlorobenzyloxycarbonyl; R⁵ is benzyl and R⁶ is benzyl and R⁷ is benzyl.

* * * * *